United States Patent
Seyed-Bolorforosh et al.

[19]

[11] Patent Number: 5,902,241
[45] Date of Patent: May 11, 1999

[54] LARGE-APERTURE IMAGING USING TRANSDUCER ARRAY WITH ADAPTIVE ELEMENT PITCH CONTROL

[75] Inventors: Mir Said Seyed-Bolorforosh, Brookfield; Anne Lindsay Hall, New Berlin; Satchidananda Panda, Greenfield, all of Wis.

[73] Assignee: General Electric Company, Milwaukee, Wis.

[21] Appl. No.: 08/977,082

[22] Filed: Nov. 24, 1997

[51] Int. Cl.$^6$ ........................................................ A61B 8/00
[52] U.S. Cl. ............................................... 600/443; 73/626
[58] Field of Search ...................................... 600/443, 447; 73/625–626; 367/7, 11, 103, 105

[56] References Cited

U.S. PATENT DOCUMENTS

| | | | |
|---|---|---|---|
| 4,215,584 | 8/1980 | Kuroda et al. | 73/626 |
| 4,641,660 | 2/1987 | Bele | 128/660 |
| 4,664,122 | 5/1987 | Yano | 600/443 |
| 5,027,820 | 7/1991 | Pesque | 128/660.07 |
| 5,083,568 | 1/1992 | Shimazaki et al. | 128/662.03 |
| 5,186,175 | 2/1993 | Hirama et al. | 128/661.01 |
| 5,278,757 | 1/1994 | Hoctor et al. | 600/459 |
| 5,301,168 | 4/1994 | Miller | 367/138 |
| 5,329,930 | 7/1994 | Thomas, III et al. | 128/661.01 |
| 5,490,512 | 2/1996 | Kwon et al. | 128/661.01 |
| 5,520,187 | 5/1996 | Snyder | 128/661.01 |
| 5,651,366 | 7/1997 | Liang et al. | 600/439 |

*Primary Examiner*—Francis J. Jaworski
*Attorney, Agent, or Firm*—Dennis M. Flaherty; Christian G. Cabou; Phyllis Y. Price

[57] ABSTRACT

An adaptive transducer array in which the element pitch is controlled by the imaging system depending on the mode of operation. A multiplicity of transducer elements are connected to a multiplicity of beamformer channels by a multiplexing arrangement having multiple states. In one multiplexer state, successive transducer elements are respectively connected to successive beamformer channels to produce an aperture having a small element pitch equal to the distance separating the centerlines of two adjacent transducer elements. In another multiplexer state, selected transducer elements are respectively connected to successive beamformer channels to produce an aperture having an increased element pitch equal to the small pitch multiplied by a factor of two or more. The aperture is increased by connecting together pairs of adjacent elements to a respective beamformer channel or by connecting every other element to a respective beamformer channel to form a sparse array.

25 Claims, 11 Drawing Sheets

PITCH = 2λ

LARGE-APERTURE IMAGING USING TRANSDUCER ARRAY WITH ADAPTIVE ELEMENT PITCH CONTROL

FIELD OF THE INVENTION

This invention generally relates to ultrasound imaging, primarily clinical ultrasound images as well as industrial ultrasonic images. In particular, the invention relates to a technique for improving the sensitivity, spatial (lateral) resolution and contrast resolution of an ultrasonic imaging system.

BACKGROUND OF THE INVENTION

Conventional ultrasound imaging systems comprise an array of ultrasonic transducer elements which are used to transmit an ultrasound beam and then receive the reflected beam from the object being studied. For ultrasound imaging, a one-dimensional array typically has a multiplicity of transducer elements arranged in a line and driven with separate voltages. By selecting the time delay (or phase) and amplitude of the applied voltages, the individual transducer elements can be controlled to produce ultrasonic waves which combine to form a net ultrasonic wave that travels along a preferred vector direction and is focused at a selected point along the beam. Multiple firings may be used to acquire data representing the same anatomical information. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. By changing the time delay and amplitude of the applied voltages, the beam with its focal point can be moved in a plane to scan the object.

The same principles apply when the transducer array is employed to receive the reflected sound (receiver mode). The voltages produced at the receiving transducers are delayed and summed so that the net signal is indicative of the ultrasound reflected from a single focal point in the object. As with the transmission mode, this focused reception of the ultrasonic energy is achieved by imparting a separate time delay (and/or phase shift) and gain to the signal from each receiving transducer.

Figure 1A:
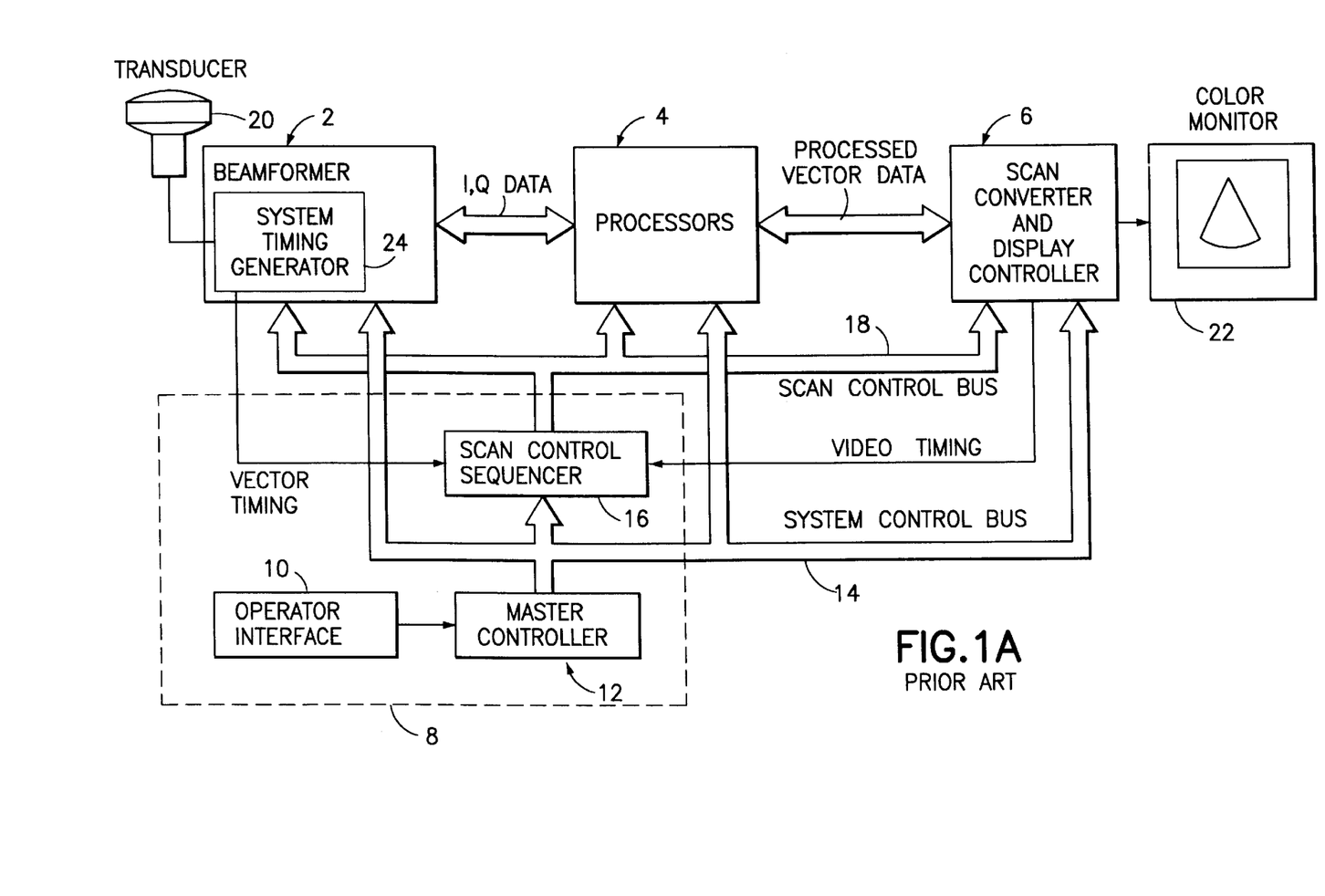
FIG. 1A is a block diagram of an ultrasound imaging system in which the present invention is incorporated.

FIG. 1A depicts an ultrasound imaging system consisting of four main subsystems: a beamformer 2, processors 4 (including a separate processor for each different mode), a scan converter/display controller 6 and a kernel 8. System control is centered in the kernel, which accepts operator inputs through an operator interface 10 and in turn controls the various subsystems. The master controller 12 performs system level control functions. It accepts inputs from the operator via the operator interface 10 as well as system status changes (e.g., mode changes) and makes appropriate system changes either directly or via the scan controller. The system control bus 14 provides the interface from the master controller to the subsystems. The scan control sequencer 16 provides real-time (acoustic vector rate) control inputs to the beamformer 2, system timing generator 24, processors 4 and scan converter 6. The scan control sequencer 16 is programmed by the host with the vector sequences and synchronization options for acoustic frame acquisitions. The scan converter broadcasts the vector parameters defined by the host to the subsystems via scan control bus 18.

The main data path begins with the analog RF inputs to the beamformer 2 from the transducer 20. The beamformer 2 outputs data to a processor 4, where it is processed according to the acquisition mode. The processed data is output as processed vector (beam) data to the scan converter/display controller 6. The scan converter accepts the processed vector data and outputs the video display signals for the image to color monitor 22.

Figure 1B:
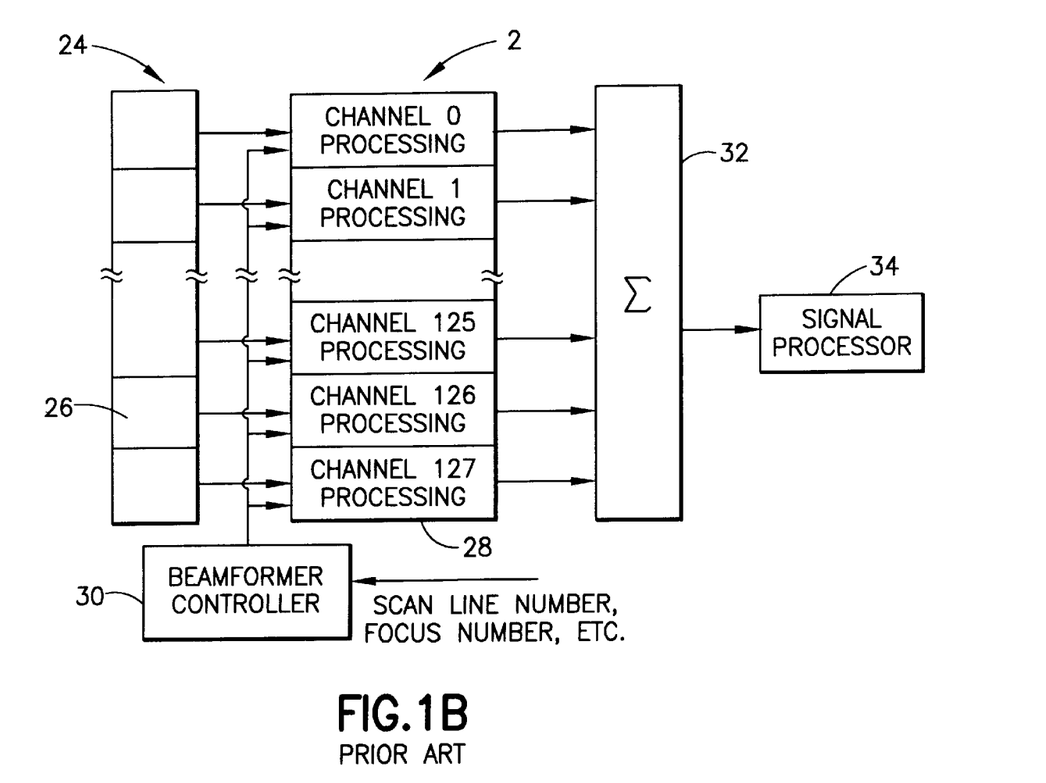
FIG. 1B is a block diagram of a typical 128-channel beamformer in a conventional ultrasound imaging system.

Referring to FIG. 1B, a conventional ultrasound imaging system includes a transducer array 24 comprised of a plurality of separately driven transducer elements 26, each of which produces a burst of ultrasonic energy when energized by a pulsed waveform produced by a transmitter (not shown). The ultrasonic energy reflected back to transducer array 24 from the object under study is converted to an electrical signal by each receiving transducer element 26 and applied separately to beamformer 2.

The echo signals produced by each burst of ultra-sonic energy reflect from objects located at successive ranges along the ultrasonic beam. The echo signals are sensed separately by each transducer element 26 and the magnitude of the echo signal at a particular point in time represents the amount of reflection occurring at a specific range. Due to the differences in the propagation paths between an ultrasound-scattering sample volume and each transducer element 26, however, these echo signals will not be detected simultaneously and their amplitudes will not be equal. Beamformer 2 amplifies the separate echo signals, imparts the proper time delay to each, and sums them to provide a single echo signal which accurately indicates the total ultrasonic energy reflected from the sample volume. Each beamformer channel 28 receives the analog echo signal from a respective transducer element 26.

To simultaneously sum the electrical signals produced by the echoes impinging on each transducer element 26, time delays are introduced into each separate beamformer channel 28 by a beamformer controller 30. The beam time delays for reception are the same delays as the transmission delays. However, the time delay of each beamformer channel is continuously changing during reception of the echo to provide dynamic focusing of the received beam at the range from which the echo signal emanates. The beamformer channels also have circuitry (not shown) for apodizing and filtering the received pulses.

The signals entering the summer 32 are delayed so that when they are summed with delayed signals from each of the other beamformer channels 28, the summed signals indicate the magnitude and phase of the echo signal reflected from a sample volume located along the steered beam. A signal processor or detector 34 converts the received signal to display data. In the B-mode (grey-scale), this would be the envelope of the signal with some additional processing such as edge enhancement and logarithmic compression. The scan converter 6 receives the display data from detector 34 and converts the data into the desired image for display. In particular, the scan converter 6 converts the acoustic image data from polar coordinate (R-θ) sector format or Cartesian coordinate linear array to appropriately scaled Cartesian coordinate display pixel data at the video rate. This scan-converted acoustic data is then output for display on display monitor 22, which images the time-varying amplitude of the envelope of the signal as a grey scale.

A phased-array ultrasound transducer consists of an array of small piezoelectric elements, with an independent electrical connection to each element. In most conventional transducers the elements are arranged in a single row, spaced at a fine pitch (one-half to one acoustic wavelength on center). As used herein, the term "1D" array refers to a single-row transducer array having an elevation aperture which is fixed and a focus which is at a fixed range; the term "1.5D" array refers to a multi-row array having an elevation aperture, shading, and focusing which are dynamically variable, but symmetric about the centerline of the array; and the term "2D" array refers to a multi-row transducer array having an elevation geometry and performance which are comparable to azimuth, with full electronic apodization, focusing and steering. Electronic circuitry connected to the elements uses time delays and perhaps phase rotations to control the transmitted and received signals and form ultrasound beams which are steered and focused throughout the imaging plane. For some ultrasound systems and probes, the number of transducer elements in the probe exceeds the number of channels of beamformer electronics in the system. In these cases an electronic multiplexer is used to dynamically connect the available channels to different (typically contiguous) subsets of the transducer elements during different portions of the image formation process.

Figure 2:
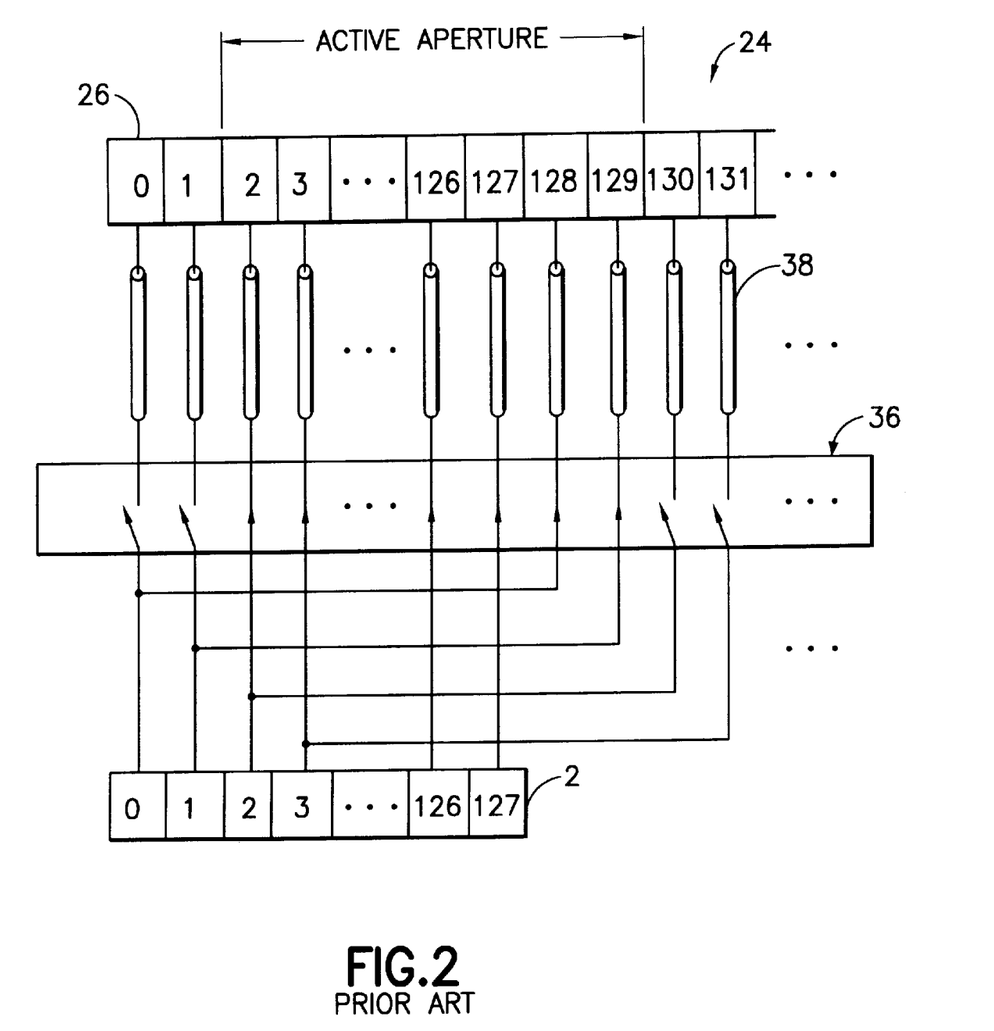
FIG. 2 is a schematic of a conventional arrangement in which a multiplexer is connected between a set of beamformer channels and a 1D transducer array having a number of elements greater than the number of beamformer channels.

A typical 1D linear or convex transducer array and multiplexer is shown schematically in FIG. 2. The beamformer 2 has 128 beamformer channels, but the transducer array 24 has significantly more elements (typically 192 to 256). The multiplexer 36 allows any set of up to 128 contiguous transducer elements 26 to be simultaneously connected to the beamformer channels 28 via coaxial cable bundles 38. By closing switches connected to elements 0 through 127, the beamformer 2 is connected to the left end of the transducer array and focused beams of ultrasound may be transmitted and received to acquire data for the corresponding edge of the image. As the point of origin of successive ultrasound beams steps along the transducer array 24 to the right, it becomes advantageous to shift the active aperture so that the origin of the ultrasound beam is centered within it. To shift the aperture from the extreme left end of the array by one element toward the right, the multiplexer switch connected to element 0 is opened and the switch connected to element 128 is closed. This shifts beamformer channel 0 from the left end to the right end of the active aperture, while leaving all other channels and elements connected as before. The time delays and other beamforming parameters are changed by the software to correspond to the new multiplexer state and one or more additional image vectors are acquired. Then the aperture is stepped further to the right, by opening the switch connected to element 1 and closing the switch connected to element 129, leaving the multiplexer 36 in the state shown in FIG. 2. In this manner the active aperture can be stepped sequentially from one end of the transducer array 24 to the other. Alternatively, the same multiplexer hardware may be used to scan the active aperture more rapidly across the array by switching several transducer elements per step. In some imaging modes, successive apertures may be selected non-sequentially, jumping back and forth between the left and right ends of the transducer array.

The spatial resolution, along the lateral axis, of a conventional ultrasound imaging system is determined by the imaging F number and the operating wavelength. A small F number, used for high-resolution imaging, requires a large aperture. The maximum aperture size is limited to the product of the element pitch and the number of channels available on the beamformer. There is a need for a technique that overcomes this limitation on maximum aperture size.

SUMMARY OF THE INVENTION

The present invention is an adaptive transducer array in which the element pitch is controlled by the imaging system depending on the mode of operation. This provides higher sensitivity together with better spatial (lateral) and contrast resolution compared to the conventional systems with constant pitch. The invention applies to all imaging modes (B, M, color, PDI and Doppler).

In accordance with the method of the present invention, aperture size is increased by increasing the pitch of a row of transducer elements. In the case of a multi-row transducer array, the pitch can be increased in more than one row. A multiplicity of transducer elements are connected to a multiplicity of beamformer channels by a multiplexing arrangement having multiple states. In one multiplexer state, successive transducer elements are respectively connected to successive beamformer channels to produce an aperture having an element pitch equal to the distance separating the centerlines of two adjacent transducer elements (hereinafter "small pitch"). In another multiplexer state, selected transducer elements are respectively connected to successive beamformer channels to produce an aperture having an increased element pitch equal to the small pitch multiplied by a factor of two or more.

Three techniques to increase the aperture are disclosed. The applications of this invention to 1.25D, 1.5D and 2D arrays are discussed. The preferred method is to connect together the adjacent elements in an array in order to form a larger active aperture by increasing the pitch. Alternatively, every other element in an array could be connected to a respective beamformer channel to form a sparse array having a larger aperture. The last method is a combination of these two techniques where the active aperture is divided into a number of segments, each segment comprising a region with small pitch, a region with larger pitch obtained by shorting adjacent elements together or a region with larger pitch obtained with sparse spacing of elements. A hybrid aperture can also be formed in which different pitches are used for different elements in an array. The element pitch can be proportional to the derivative of the beamformer delay profile across the given aperture. The distribution of the three types of segments depends on the aperture design constraints.

The method for selectively increasing the element pitch of the transducer array in accordance with the invention improves the beam profile at the deeper depths, by providing a larger aperture. It also increases the two-way sensitivity of the array in the far field.

Furthermore, since the transmit and receive center frequency typically changes as a function of the imaging depth, it requires a method to adaptively change the transducer pitch. This ensures that the transducer pitch remains a constant number of wavelengths for all imaging frequencies for the given transducer. Using this scheme, fine pitch is used for imaging at higher frequencies. When operating at lower frequencies, the larger pitch can be used.

BRIEF DESCRIPTION OF THE DRAWINGS

FIGS. 3A–3D are schematics showing different aperture functions for a transducer array in accordance with the present invention.

3B shows an array with adjacent elements connected.

DETAILED DESCRIPTION OF THE PREFERRED EMBODIMENTS

Figure 3A:
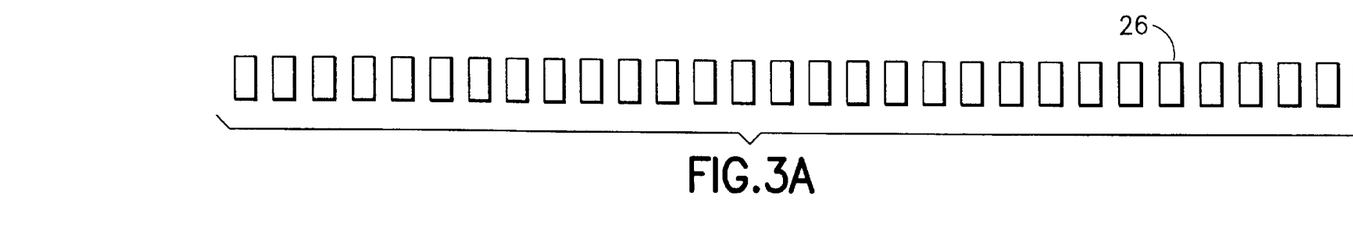
FIG. 3A shows a conventional array; FIG.
Figure 3B:
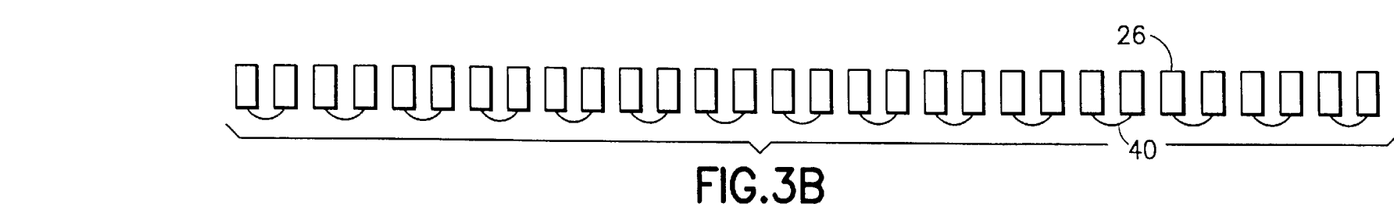
Figure 3C:
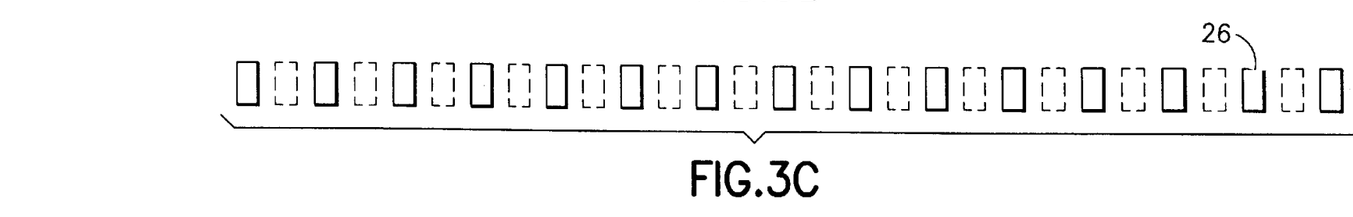
FIG. 3C shows a sparse array.

In accordance with the method of the present invention, a multiplicity of transducer elements is connected to a multiplicity of beamformer channels by a multiplexing arrangement having multiple states. In one multiplexer state, successive transducer elements are respectively connected to successive beamformer channels to produce an aperture having a small pitch equal to the distance separating the centerlines of two adjacent transducer elements. This multiplexer state is depicted schematically in FIG. 3A, which shows a conventional array of equally spaced elements having an element pitch P. In other multiplexer states, selected transducer elements are respectively connected to successive beamformer channels to produce an aperture having an increased element pitch equal to (n×P), where n is a positive integer greater than unity. FIGS. 3B and 3C show other multiplexer states for n=2.

In accordance with the preferred embodiment shown in FIG. 3B, in one multiplexer state the array acts in a conventional manner with pitch P and in another multiplexer state the pitch is increased to 2P by selectively connecting together adjacent transducer elements 26 in the array, in effect, to form wider transducer elements. For example, each successive pair of adjacent transducer elements in a row can be shorted together and connected to a respective beamformer channel for activation. These connections are indicated by lines 40. This technique of increasing the pitch can be extrapolated by shorting groups of three or more adjacent transducer elements in a row.

In accordance with the preferred embodiment shown in FIG. 3C, in one multiplexer state the array acts in a conventional manner with pitch P and in another multiplexer state the pitch is increased to 2P by selectively connecting only a subset of the transducer elements in the array to the beamformer channels for activation. For example, instead of connecting every transducer element to a respective beamformer channel, only every other transducer element in the array is connected to a respective channel to form a larger active aperture. This sparse array is depicted in FIG. 3C. Unactivated elements are indicated by dashed rectangles; activated elements are indicated by solid rectangles. This technique of increasing the pitch can be extrapolated by activating every third or more transducer element in a row.

Figure 3D:
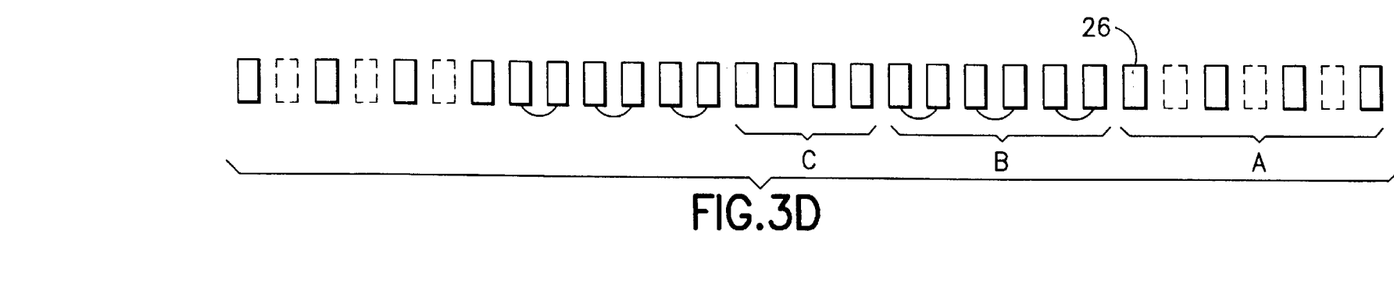
FIG. 3D shows a hybrid array. The gaps between adjacent elements are exaggerated in size for the purpose of illustration.

In accordance with yet other preferred embodiments of the invention, the pitch is increased using a combination of the above-described techniques. The active aperture is divided into a plurality of segments. In accordance with the preferred embodiment depicted in FIG. 3D, the multiplexing arrangement is designed so that a first set of segments each include transducer elements which can be activated in accordance with either the small-pitch multiplexer state or a larger-pitch multiplexer state which shorts adjacent elements together; and a second set of array segments each include transducer elements which can be activated in accordance with either the small-pitch multiplexer state or a larger-pitch multiplexer state which produces sparse spacing of activated elements. In accordance with a further variation, a third set of array segments can be incorporated in the array, each array segment in the third set consisting of transducer elements having the small pitch only. FIG. 3D shows an array having a multiplexer state such that the elements in the near-field aperture formed by segment C have pitch P; the elements in the mid-field aperture formed by segments B on either side of segment C are shorted in pairs to provide a pitch equal to 2P; and the elements in the far-field aperture formed by segments A and form sparse arrays of pitch 2P. The distribution of the above-described segments in an ultrasonic transducer array will depend on the aperture design constraints, such as the beamformer delay profile.

Figure 4:
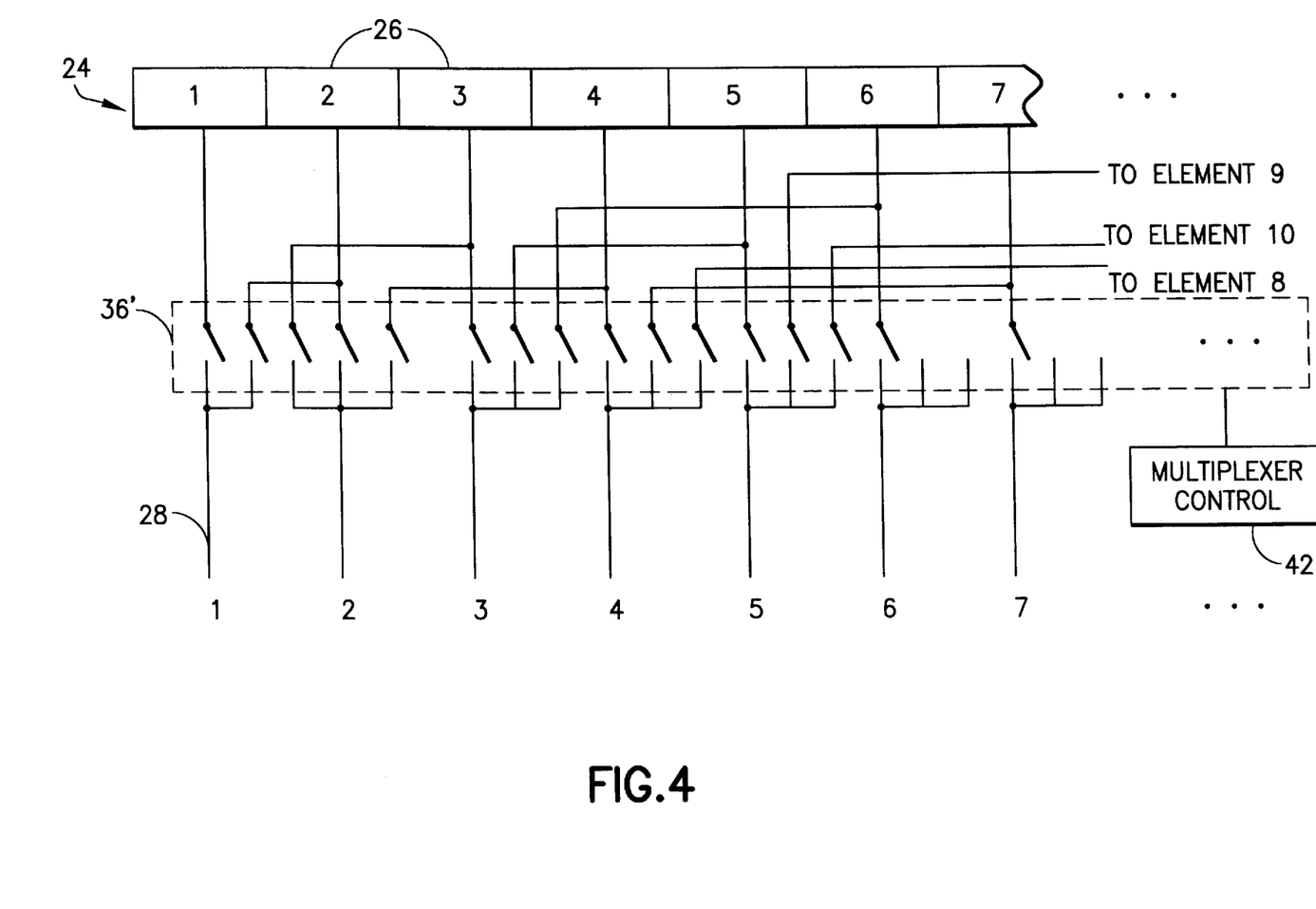
FIG. 4 is a schematic of a multiplexing arrangement in accordance with one preferred embodiment of the invention.

FIG. 4 shows a multiplexer 36' which allows the transducer elements 26 to be connected to the beamformer channels 28 in any of three multiplexer states. To produce a pitch P, the switches connecting the n-th element to the n-th channel are closed and the remaining switches are open. To produce a pitch 2P by shorting pairs of elements together, the switches connecting the (2n−1)-th and (2n)-th elements to the n-th channel are closed and the remaining switches are open. To produce a pitch 2P using a sparse array, the switches connecting the (2n−1)-th element to the n-th channel are closed and the remaining switches are open. The state of multiplexer 36' is controlled by a multiplexer control board 42. The control board 42 receives a MUX State command from the master controller 12 (see FIG. 1A) and uses data stored in on-board memory (ROM or EEPROM) to set every switch in multiplexer 36' to the open or closed position required for the commanded multiplexer state.

Figure 5:
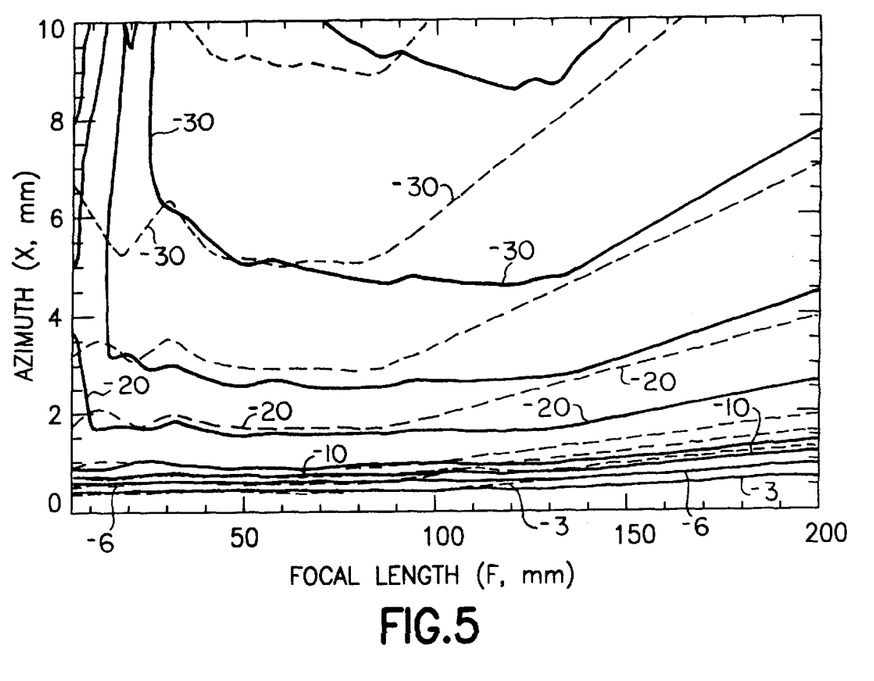
FIGS. 5 and 6 are graphs showing the radiation pattern and pressure as a function of depth (mm) (oneway response) for the two transducer arrays with smallpitch (dashed lines) and large-pitch (solid lines) aperture functions as depicted in FIGS. 3A and 3B respectively.

In order to demonstrate the effect of the small F number obtained by electrically connecting the adjacent elements in an array, the azimuthal beam profiles of three arrays were simulated. This was done by applying the Rayleigh Summerfield diffraction integral which performs a full analysis of the diffraction profile. A dynamic receive beamformer was simulated. Three arrays were compared. The first array had 128 elements with a small pitch. The second array had a pitch which is twice the pitch of the first array but with 96 elements only. This represents the array elements being connected together. The 96 elements correspond to an array with 192 elements whereby the adjacent elements are connected together. The receive F number was set to F1. FIG.

5 shows the improved beam profile at −3, −6, −10, −20 and −30 dB using the array with larger aperture. Hence the larger aperture improves the lateral beam profile of the array in the far field.

Figure 6:
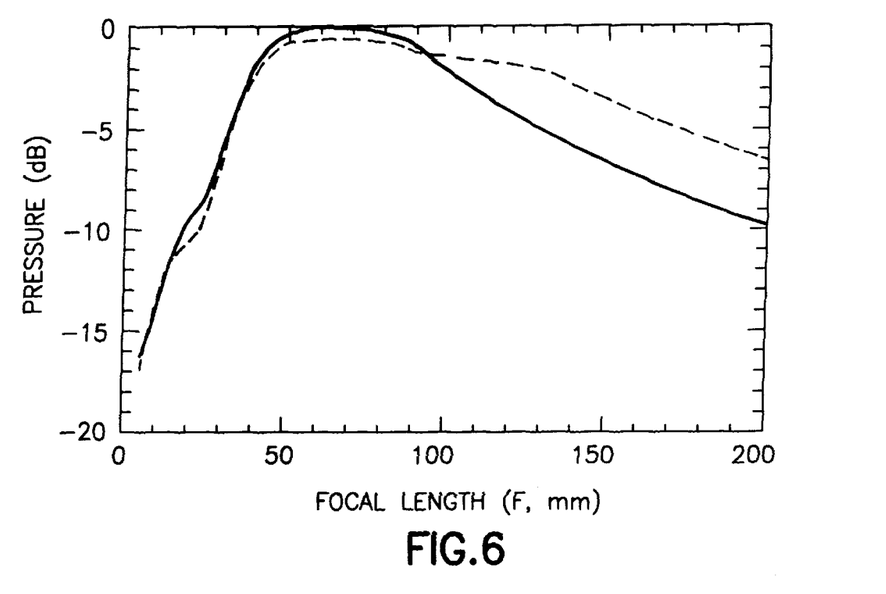

The larger aperture obtained by connecting adjacent elements together also provides higher sensitivity due to the increase in aperture size and increase in the surface area of the receiver and transmitter. This is confirmed by the Rayleigh diffraction integral calculations as shown in FIG. 6, which shows that up to the point where the two arrays have the same aperture size, the sensitivity is almost equal. However, once the signal goes beyond 100 mm, the array with the larger aperture, and greater pitch, provides higher sensitivity. The results shown in FIGS. 5 and 6 are both one-way responses. At deeper depths up to +6 dB (two way), improvements in the sensitivity can be obtained due to the increased aperture size. A further sensitivity improvement is expected if 128 joined elements are used to form the aperture instead of the 96 joined elements used in this example.

Figure 7:
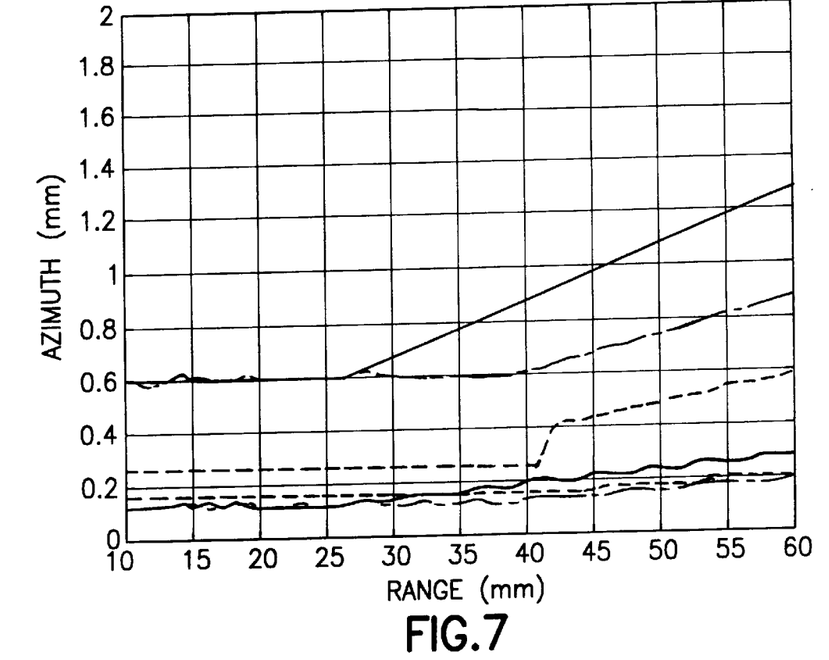
FIGS. 7 and 8 are respective graphs showing the radiation pattern and pressure as a function of depth (mm) (one-way response) for three transducer arrays with a small aperture of 128 elements (solid lines); 96 shorted elements (dashed lines); and 96 elements in a sparse array (dotted lines) as depicted in FIGS. 3A–3C respectively.
Figure 8:
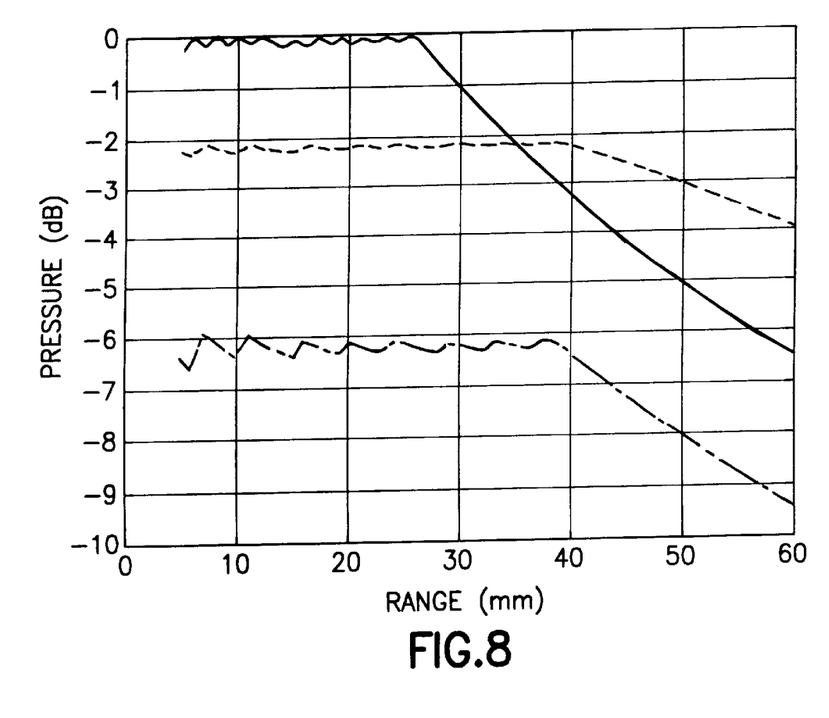

A similar calculation was performed which compared the performance of a conventional (small pitch) 128-element array, an array of 192 elements shorted to form 96 wider elements and a 96-element sparse array. The oneway −6 and −20 dB beam profiles for these three transducers are shown in FIG. 7. Notice the improved reduction in the size of the main beam and side lobes down to −40 dB two-way response. The one-way pressure response is also shown as a function of depth (range) in FIG. 8. The sensitivity is improved using the array with the adjacent elements shorted together. Using this scheme if the element widths are sufficiently small, even more than two adjacent elements can be joined to form an even bigger aperture size.

The element pitch control scheme of the present invention can be applied adaptively to different scan types during both transmit and receive. Three examples are given here. When the beam is steered, the smaller pitch can be used for better element directivity. However, when firing the A-lines straight ahead, the element pitch can be increased for improved aperture size. One such example is in the case of B-mode sector scans (i.e., virtual apex) using linear arrays. In this case when the A-lines at the edge of the array are fired, the finer pitch is used. However, when firing the A-lines which are directed straight ahead, the larger element pitch is used. Another example of this scheme is in the case of sparse arrays. In the case of sparse arrays the grating lobe is going to be larger than conventional arrays or arrays with the adjacent elements connected together. Hence the larger pitch obtained by sparse arrays, used for larger aperture, can be used only when in the zoom mode where the grating lobes are not going to be displayed in the main region of interest. As will be shown hereinafter, using a hybrid aperture function, the level of signal in the grating lobes can be reduced compared to the sparse array. Different combinations of the proposed aperture functions can be used during transmit and receive depending on the system architecture or the imaging mode.

In accordance with further variations of the invention, different criteria can be used to control the effective pitch of the elements in an array. The pitch selection can depend on the beamformer delay difference across adjacent elements. In this case, for a given delay profile where the differential time delay is large across two adjacent elements, a smaller pitch is used and vice versa. This scheme adjusts the pitch of elements to utilize all of the available elements in a given transducer while providing a small beamformer phase error across the aperture.

There are two advantages in shorting the adjacent elements together instead of driving them in a sparse array format. First, the level of energy in the grating lobes is reduced when the elements are shorted together as compared to the sparse array. Second, the array sensitivity is higher when the elements are connected together due to the increase in the receiver and transmitter surface area.

Figure 9A:
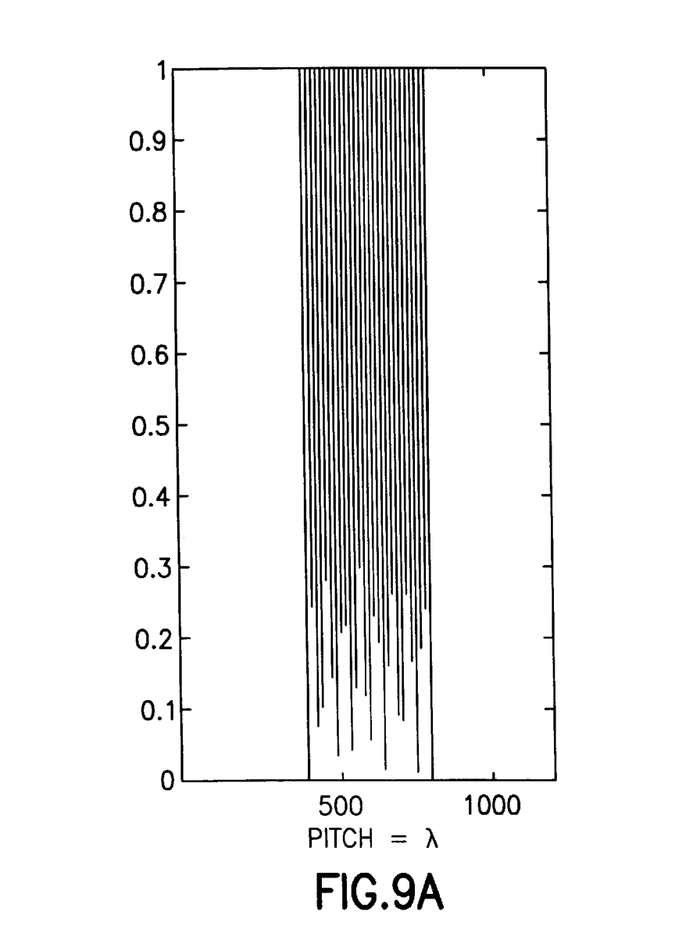
FIGS. 9A and 9B are graphs showing the aperture function (amplitude versus spatial position) and the far-field radiation pattern (amplitude versus angle ×10) for the transducer array of FIG. 3B.
Figure 9B:
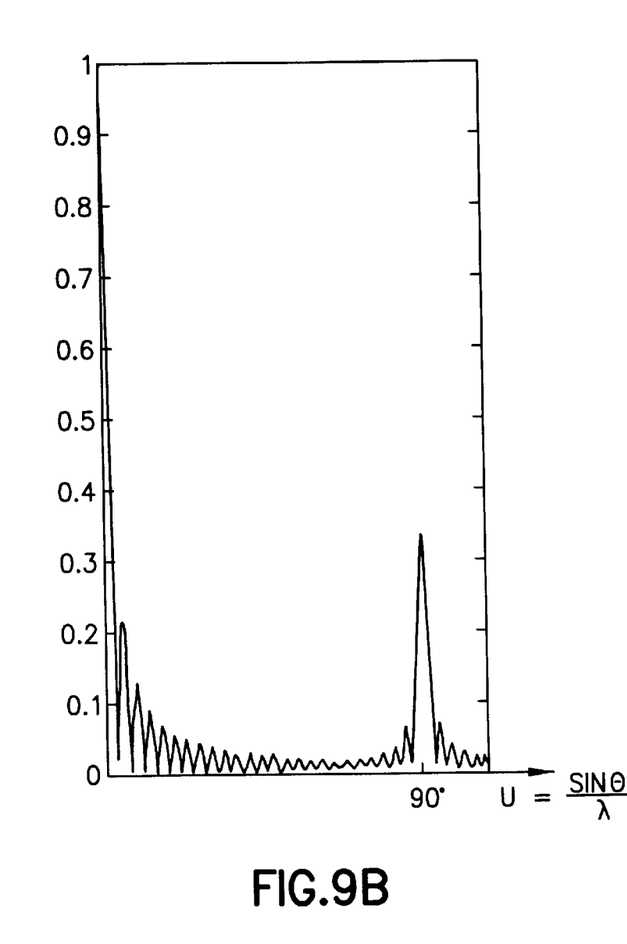
Figure 10A:
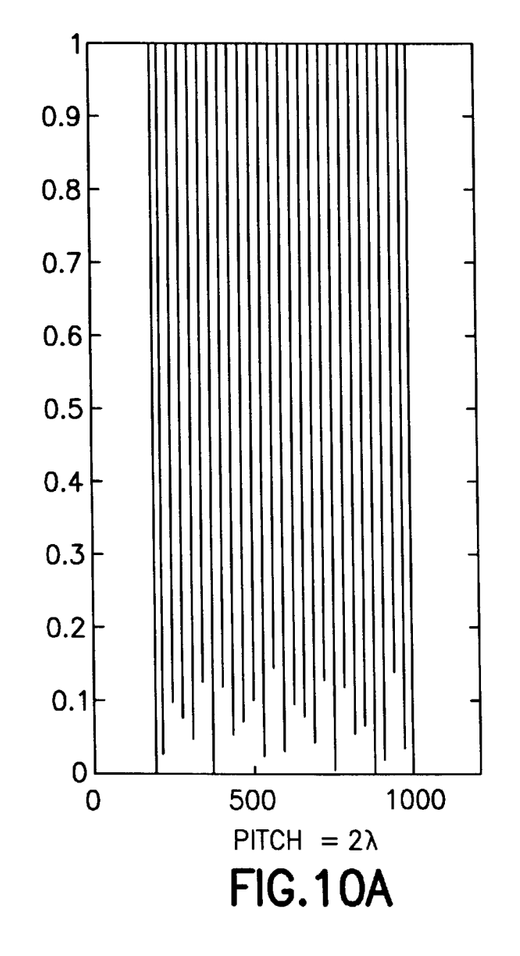
FIGS. 10A and 10B are graphs showing the aperture function (amplitude versus spatial position) and the far-field radiation pattern (amplitude versus angle ×10) for the sparse array of FIG. 3C.
Figure 10B:
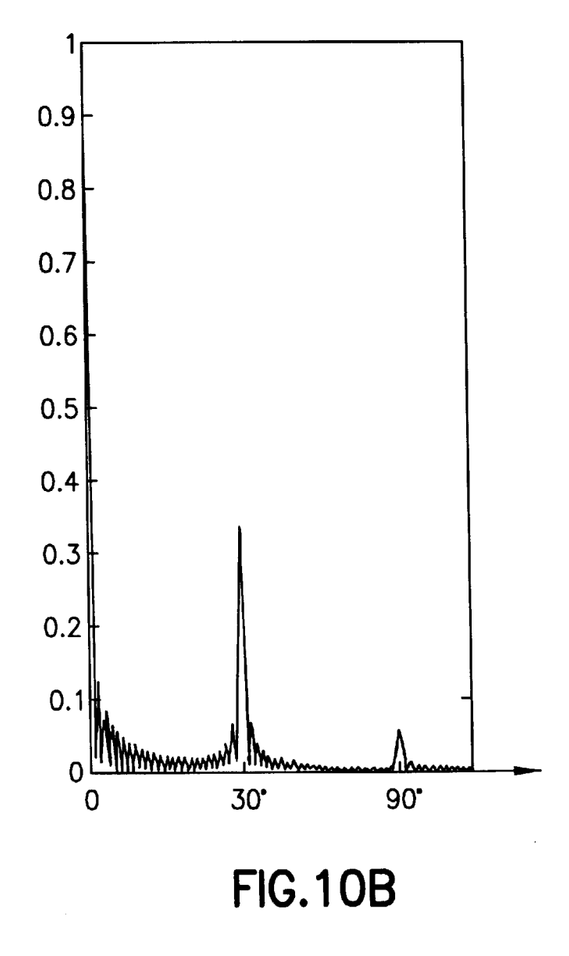
Figure 11A:
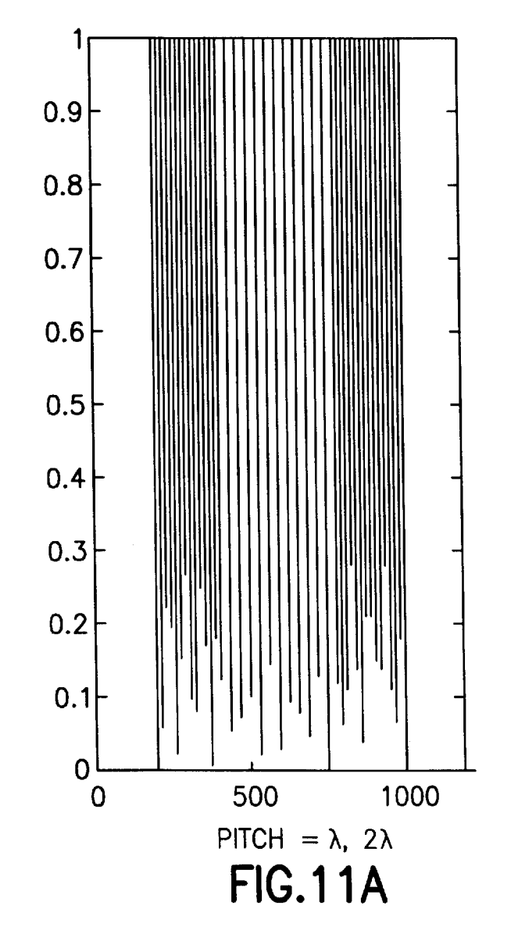
FIGS. 11A and 11B are graphs showing the aperture function (amplitude versus spatial position) and the far-field radiation pattern (amplitude versus angle ×10) for the hybrid array of FIG. 3D.
Figure 11B:
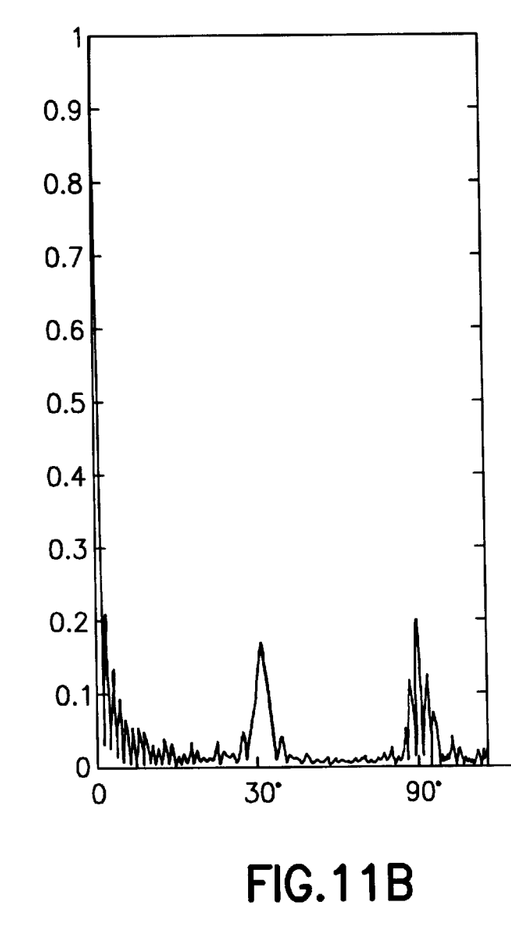

In the first case an array with small aperture and small pitch (see FIG. 9A) was examined which demonstrated conventional aperture functions. The far-field CW radiation pattern in such an array is shown in FIG. 9B. Next the aperture size is increased in order to form a sparse array (see FIG. 10A). The width of the main beam is reduced as seen in FIG. 10B. However, if FIGS. 9B and 10B are compared, it can be seen that the grating lobes became closer to the main beam for the sparse array. This is a typical characteristic of sparse arrays. Next a hybrid array which has a small pitch at the edges and a large pitch at the center of the array was examined (see FIG. 11A). In this case the width of the main beam and the position of the side lobes (see FIG. 11B) are similar to the those of a sparse array with large aperture size. However, the energy in the first grating lobe is reduced compared to the sparse array. Hence using the hybrid aperture function, the entire channels of the system are utilized while maximizing the aperture size with reduced signal level in the grating lobes compared to the pure sparse array.

Figure 12:
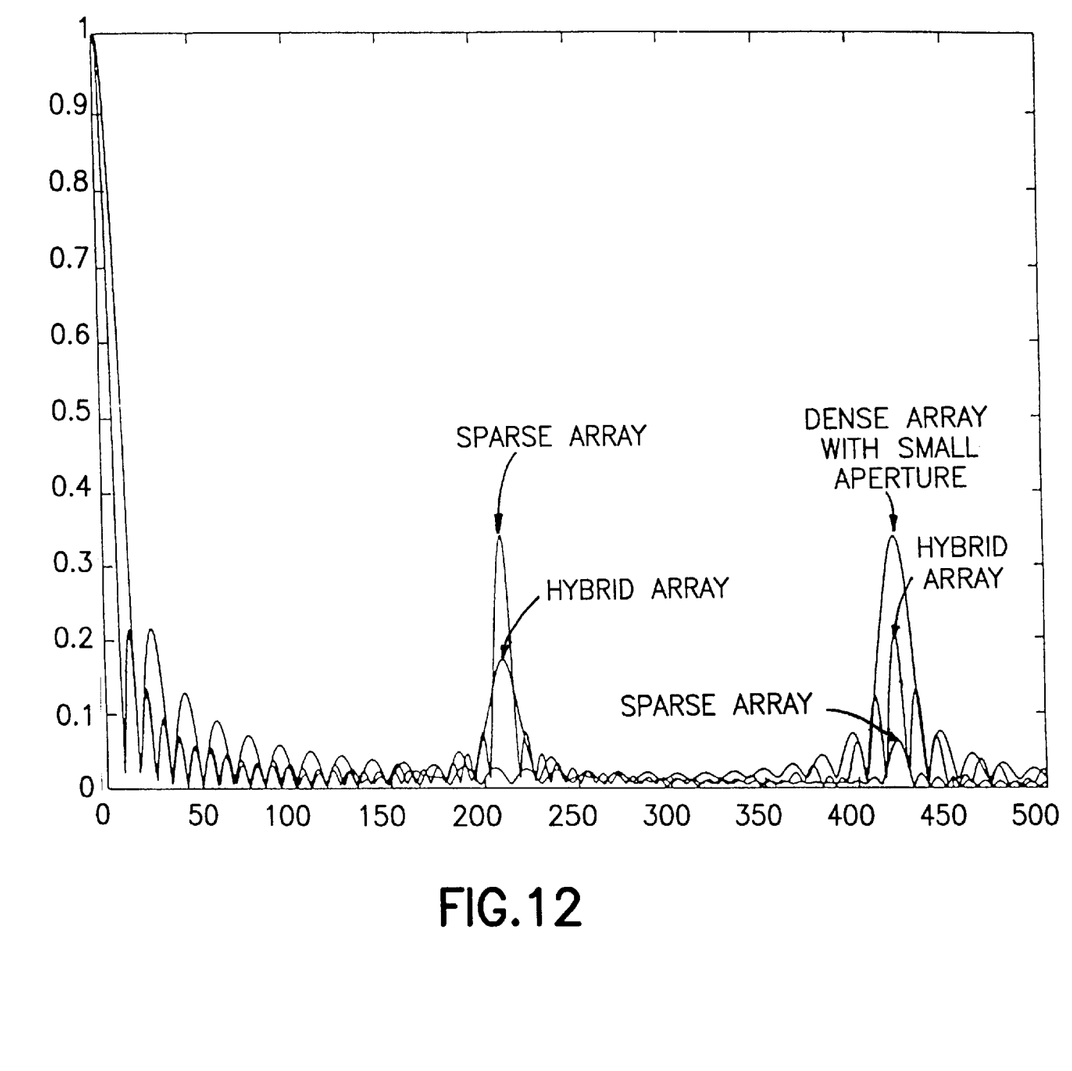
FIG. 12 is a graph showing a magnified image of the far-field radiation patterns shown in FIGS. 9B, 10B and 11B.

There is also an advantage in having a hybrid array compared to all other configurations. The hybrid array has a lower grating lobe level while maintaining a small main beam width. This is illustrated in FIG. 12. The energy in the grating lobes of the hybrid array is controlled by the percentage of the aperture which has a large spatial sampling.

Another application of adaptive pitch control would be for 1.5D or 2D arrays where the number of transducer elements often exceeds the number of available beamformer channels. By shorting adjacent transducer elements, along the elevation or azimuth planes, more elements can be used to form the active aperture. For example, a reduction by a factor of 3 in any row or column for a 2D array can result in a reduction by a factor of 9 in the total number of system channels, while maintaining a large overall aperture for a small F number. For a 60×60 2D array, this would reduce the system channels from 3600 to 400, which is a significant reduction. This concept can also be applied to groups larger than three elements to further reduce the number of desired channels.

A mixed group of elements comprising single elements, pairs of shorted elements, triplets of shorted elements or larger groups of shorted elements can be used to provide different pitches to give a desired response. Certain criteria can be established for the side lobe level, main beam width and grating lobe level while using adaptive methods to determine the optimum aperture function. This concept can be further expanded to include the effect of having different transmit and receive apertures functions.

This concept can also be applied to "theta" arrays, i.e., arrays comprising a linear row of transducer elements surrounded by an elliptical ring of transducer elements. Different constraints can be used to define which elements are shorted together.

Another application for the present invention is for non-linear harmonic imaging. In this mode of imaging, the signal is transmitted at lower frequency while the larger pitch is used. During reception, the first harmonic signal generated due to non-linear ultrasound propagation is used for detection. The received signal is at a frequency which is twice the transmission frequency. The finer pitch is used to form the aperture which is used for detection of the signal.

The foregoing preferred embodiments have been disclosed for the purpose of illustration. Variations and modifications will be readily apparent to those skilled in the art. For example, the element pitch of the transducer elements connected to beamformer channels by closed switches can be changed as a function of the overall aperture size, the operating frequency or the steering angle. In addition, it will be apparent that the above-described techniques have application when ultrasound beams are generated using different aperture configurations to form a synthetic aperture which combines the characteristics of different aperture functions. All such variations and modifications are intended to be encompassed by the claims set forth hereinafter.

We claim:

1. An ultrasound imaging system comprising,
    a beamformer comprising a multiplicity of N beamformer channels;
    a transducer array comprising a multiplicity of M piezoelectric transducer elements, where $M \geq N$;
    switching means for multiplexing imaging data between said M piezoelectric transducer elements and said N beamformer channels;
    control means for selectively configuring said switching means to have first and second switching states in response to receipt of first and second switching state commands, respectively; and
    means for changing the element pitch of the transducer elements connected to beamformer channels as a function of the operating frequency,
    wherein in said first switching state, N successive transducer elements are connected by closed switches to said N beamformer channels in 1-to-1 relationship, and in said second switching state, N successive groups of transducer elements, each group consisting of x transducer elements, are connected by closed switches to said N beamformer channels in x-to-1 relationship, wherein x is an integer greater than or equal to 2.

2. A method for transmitting ultrasound beams from a transducer array connected to a beamformer, the beamformer comprising a multiplicity of N beamformer channels, and the transducer array comprising a multiplicity of M piezoelectric transducer elements physically spaced at constant element pitch P, where $M \geq N$, comprising the steps of:
    activating a first set of said multiplicity of transducer elements to transmit a first ultrasound beam, said first set of activated transducer elements having said element pitch P;
    activating a second set of said multiplicity of transducer elements to transmit a second ultrasound beam, wherein said second set has an element pitch xP and comprises a plurality of groups of transducer elements, each group consisting of x adjacent transducer elements which are shorted together, wherein x is an integer greater than or equal to 2; and
    activating a third set of said multiplicity of transducer elements to transmit a third ultrasound beam, said third set having an element pitch yP and comprising a plurality of non-adjacent transducer elements having constant spacing, each pair of activated transducer elements of said constant spacing being separated by (y−1) non-activated transducer elements, wherein y is an integer greater than or equal to 2.

3. An ultrasound imaging system comprising:
    a beamformer comprising a multiplicity of N beamformer channels;
    a transducer array comprising a multiplicity of M piezoelectric transducer elements, where $M \geq N$;
    first means for activating a first set of said multiplicity of transducer elements to transmit a first ultrasound beam, said first set of activated transducer elements having said element pitch P;
    second means for activating a second set of said multiplicity of transducer elements to transmit a second ultrasound beam, wherein said second set has an element pitch xP and comprises a plurality of groups of transducer elements, each group consisting of x adjacent transducer elements which are shorted together, wherein x is an integer greater than or equal to 2; and
    third means for activating a third set of said multiplicity of transducer elements to transmit a third ultrasound beam, said third set having an element pitch yP and comprising a plurality of non-adjacent transducer elements having constant spacing, each pair of activated transducer elements of said constant spacing being separated by (y−1) non-activated transducer elements, wherein y is an integer greater than or equal to 2.

4. The ultrasound imaging system as defined in claim 3, wherein said first, second and third sets of activated transducer elements are used in the same aperture.

5. The ultrasound imaging system as defined in claim 3, further comprising switching means for multiplexing imaging data between said M piezoelectric transducer elements and said N beamformer channels, wherein said first activating means comprise first control means for configuring said switching means to have a first switching state; said second activating means comprise second control means for configuring said switching means to have a second switching state different than said first switching state, and said third activating means comprise third control means for configuring said switching means to have a third switching state different than each of said first and second switching states.

6. An ultrasound imaging system comprising:
    a beamformer comprising a multiplicity of beamformer channels;
    a transducer array comprising a multiplicity of piezoelectric transducer elements;
    a multiplicity of switches for multiplexing imaging data between said piezoelectric transducer elements and said beamformer channels; and
    a controller for selectively configuring said multiplicity of switches to have first and second switching states in response to receipt of first and second switching state commands, respectively,
    wherein in said first switching state, said transducer elements are electrically connected by closed switches to said beamformer channels in 1-to-1 relationship and are not electrically connected by closed switches to each other, and in said second switching state, said transducer elements are electrically connected by closed switches to at least one adjacent transducer element to form respective groups of transducer elements, and each of said groups being electrically connected by closed switches to said beamformer channels in 1-to-1 relationship.

7. The ultrasound imaging system as recited in claim 6, wherein each of said groups consists of x transducer elements electrically connected to each other and to a respective beamformer channel in x-to-1 relationship, wherein x is an integer greater than or equal to 2.

8. The ultrasound imaging system as recited in claim 7, wherein said controller further selectively configures said multiplicity of switches to have a third switching state in response to receipt of a third switching state command such that in said third switching state, the (xn−1)-th transducer element is connected by a closed switch to the n-th beamformer channel in 1-to-1 relationship.

9. The ultrasound imaging system as recited in claim 8, further comprising means for changing the element pitch of the transducer elements connected to beamformer channels as a function of the steering angle.

10. The ultrasound imaging system as recited in claim 8, further comprising means for setting the element pitch of the transducer elements connected to beamformer channels to be proportional to the derivative of the beamformer delay.

11. The ultrasound imaging system as recited in claim 6, wherein said controller is programmed to use a relatively larger element pitch for transmission of a transmit beam having a fundamental frequency and a relatively smaller element pitch for reception of a receive beam, further comprising means for detecting harmonic signal components in said receive beam.

12. The ultrasound imaging system as recited in claim 6, wherein said multiplicity of piezoelectric transducer elements are arranged in a line.

13. The ultrasound imaging system as recited in claim 6, further comprising means for changing the element pitch of the transducer elements connected to beamformer channels as a function of the overall aperture size.

14. The ultrasound imaging system as recited in claim 6, further comprising means for changing the element pitch of the transducer elements connected to beamformer channels as a function of the operating frequency.

15. The method as recited in claim 11, wherein said second transmit aperture comprises a plurality of non-adjacent transducer elements having constant spacing, each pair of activated transducer elements of said constant spacing being separated by (x−1) non-activated transducer elements, where x is an integer greater than or equal to 2.

16. The method as recited in claim 11, wherein said first beam is steered at a non-zero angle relative to a normal to the transducer array and said second beam is transmitted normal to the transducer array.

17. The method as recited in claim 11, wherein said first beam is focused at shallower depth using excitation waveforms having a relatively higher frequency and said second beam is focused at deeper depth using excitation waveforms having a relatively lower frequency.

18. An ultrasound imaging system comprising:
a beamformer comprising a multiplicity of beamformer channels;
a transducer array comprising a multiplicity of piezoelectric transducer elements;
first transmit beamforming means for driving transducer elements forming a first transmit aperture with excitation waveforms to form a first beam, said driven transmit elements of said first transmit aperture having a first element pitch;
first receive beamforming means for forming a first beamsummed signal from a first set of signals transduced by transducer elements forming a first receive aperture following transmission of said first beam;
second transmit beamforming means for driving transducer elements forming a second transmit aperture with excitation waveforms to form a second beam, said driven transmit elements of said second transmit aperture having a second element pitch greater than said first element pitch;
second receive beamforming means for forming a second beamsummed signal from a second set of signals transduced by transducer elements forming a second receive aperture following transmission of said second beam;
processing means for forming first and second image signals which are respective functions of said first and second beamsummed signals; and
a display subsystem for displaying an image having first and second image portions which are respective functions of said first and second image signals.

19. The ultrasound imaging system as recited in claim 18, further comprising:
a multiplicity of switches for multiplexing imaging data between said piezoelectric transducer elements and said beamformer channels; and
a controller for selectively configuring said multiplicity of switches to have first and second switching states in response to receipt of first and second switching state commands, respectively, said first switching state being in effect during transmission of said first beam and said second switching state being in effect during transmission of said second beam,
wherein in said first switching state, said transducer elements are electrically connected by closed switches to said beamformer channels in 1-to-1 relationship and are not electrically connected by closed switches to each other, and in said second switching state, said transducer elements are electrically connected by closed switches to at least one adjacent transducer element to form respective groups of transducer elements, and each of said groups being electrically connected by closed switches to said beamformer channels in 1-to-1 relationship.

20. The ultrasound imaging system as recited in claim 18, further comprising:
a multiplicity of switches for multiplexing imaging data between said piezoelectric transducer elements and said beamformer channels; and
a controller for selectively configuring said multiplicity of switches to have first and second switching states in response to receipt of first and second switching state commands, respectively, said first switching state being in effect during transmission of said first beam and said second switching state being in effect during transmission of said second beam,
wherein in said first switching state, said transducer elements are electrically connected by closed switches to said beamformer channels in 1-to-1 relationship and are not electrically connected by closed switches to each other, and in said second switching state, the (xn−1)-th transducer element is connected by a closed switch to the n-th beamformer channel in 1-to-1 relationship, wherein x is an integer greater than or equal to 2.

21. A method for operating an ultrasound imaging system having an array of transducer elements, comprising the steps of:
selecting transducer elements to form a transmit aperture having a first element pitch;
driving said transducer elements forming said transmit aperture with excitation waveforms having a fundamental frequency to form a transmit beam;
selecting transducer elements to form a receive aperture having a second element pitch less than said first element pitch;

forming a receive beam signal from a set of signals transduced by said transducer elements forming said receive aperture following transmission of said transmit beam;

detecting a harmonic signal component in said receive beam signal;

forming an image signal which is a function of said harmonic signal component; and displaying an image having an image portion which is a function of said image signal.

22. An ultrasound imaging system comprising:

a beamformer comprising a multiplicity of beamformer channels;

a transducer array comprising a multiplicity of piezoelectric transducer elements;

transmit beamforming means for driving transducer elements forming a transmit aperture with excitation waveforms having a fundamental frequency to form a transmit beam, said transmit aperture having a first element pitch;

receive beamforming means for forming a receive beam signal from a set of signals transduced by transducer elements forming a receive aperture following transmission of said transmit beam, said receive aperture having a second element pitch less than said first element pitch;

means for detecting a harmonic signal component in said receive beam signal;

processing means for forming an image signal which is a function of said harmonic signal component; and a display subsystem for displaying an image having an image portion which is a function of said image signal.

23. The ultrasound imaging system as recited in claim 22, further comprising:

a multiplicity of switches for multiplexing imaging data between said piezoelectric transducer elements and said beamformer channels; and a controller for selectively configuring said multiplicity of switches to have first and second switching states in response to receipt of first and second switching state commands, respectively, said first switching state being in effect during transmission of said transmit beam and said second switching state being in effect during reception of said receive beam, wherein in said second switching state, said transducer elements are electrically connected by closed switches to said beamformer channels in 1-to-1 relationship and are not electrically connected by closed switches to each other, and in said first switching state, said transducer elements are electrically connected by closed switches to at least one adjacent transducer element to form respective groups of transducer elements, and each of said groups being electrically connected by closed switches to said beamformer channels in 1-to-1 relationship.

24. The ultrasound imaging system as recited in claim 22, further comprising:

a multiplicity of switches for multiplexing imaging data between said piezoelectric transducer elements and said beamformer channels; and a controller for selectively configuring said multiplicity of switches to have first and second switching states in response to receipt of first and second switching state commands, respectively, said first switching state being in effect during transmission of said transmit beam and said second switching state being in effect during reception of said receive beam, wherein in said second switching state, said transducer elements are electrically connected by closed switches to said beamformer channels in 1-to-1 relationship and are not electrically connected by closed switches to each other, and in said first switching state, the (xn−1)-th transducer element is connected by a closed switch to the n-th beamformer channel in 1-to-1 relationship, wherein x is an integer greater than or equal to 2.

25. A method for operating a transducer array to transmit beams of wave energy, comprising the steps of:

opening a switch to electrically disconnect a first transducer element of said transducer array from a second transducer element of said transducer array;

driving said first transducer element with a first excitation waveform during a first transmit firing;

driving said second transducer element with a second excitation waveform during said first transmit firing;

closing said switch to electrically connect said first transducer element to said second transducer element; and driving said first and second transducer elements with a third excitation waveform during a second transmit firing.

* * * * *